United States Patent
Nørgaard et al.

(10) Patent No.: US 12,150,782 B2
(45) Date of Patent: *Nov. 26, 2024

(54) EAR PROBE FOR HEARING TESTING

(71) Applicant: Interacoustics A/S, Middelfart (DK)

(72) Inventors: Kren Rahbek Nørgaard, Middelfart (DK); Pete Bray, Middelfart (DK); Hicham Saoud, Middelfart (DK)

(73) Assignee: Interacoustics A/S, Middelfart (DK)

( * ) Notice: Subject to any disclaimer, the term of this patent is extended or adjusted under 35 U.S.C. 154(b) by 167 days.

This patent is subject to a terminal disclaimer.

(21) Appl. No.: 17/883,929

(22) Filed: Aug. 9, 2022

(65) Prior Publication Data

US 2022/0378331 A1    Dec. 1, 2022

Related U.S. Application Data (63) Continuation of application No. 15/840,299, filed on Dec. 13, 2017, now Pat. No. 11,439,349.

(30) Foreign Application Priority Data

Dec. 14, 2016    (EP) .................................. 16204046

(51) Int. Cl.
| | | |
|---|---|---|
| *A61B 5/00* | (2006.01) | |
| *A61B 5/12* | (2006.01) | |
| *H04R 1/02* | (2006.01) | |
| *H04R 1/08* | (2006.01) | |

(52) U.S. Cl.
CPC .............. *A61B 5/6803* (2013.01); *A61B 5/12* (2013.01); *A61B 5/125* (2013.01); *A61B 5/6817* (2013.01); *A61B 5/6887* (2013.01); *H04R 1/028* (2013.01); *H04R 1/08* (2013.01); *A61B 2560/0443* (2013.01); *A61B 2562/0204* (2013.01)

(58) Field of Classification Search
CPC ......... A61B 5/6803; A61B 5/12; A61B 5/125; A61B 5/6817; A61B 5/6887; A61B 2560/0443; A61B 2562/0204; H04R 1/028; H04R 1/08
USPC ....................................................... 600/559
See application file for complete search history.

(56) References Cited

U.S. PATENT DOCUMENTS

| | | |
|---|---|---|
| 3,882,848 A | 5/1975 | Klar et al. |
| 4,057,051 A | 11/1977 | Kerouac |
| 6,126,614 A | 10/2000 | Jenkins et al. |
| 9,629,575 B2 | 4/2017 | Geertsen |
| 2004/0171966 A1 | 9/2004 | Iseberg |
| 2007/0161924 A1 | 7/2007 | Dolphin et al. |
| 2012/0191004 A1 | 7/2012 | Iseberg et al. |

(Continued)

FOREIGN PATENT DOCUMENTS

| | | |
|---|---|---|
| JP | 2016-135238 A | 7/2016 |
| WO | WO2016/145522 A1 | 9/2016 |

*Primary Examiner* — Eric J Messersmith
*Assistant Examiner* — Chanel J Jhin
(74) *Attorney, Agent, or Firm* — Birch, Stewart, Kolasch & Birch, LLP (57) ABSTRACT

An ear probe assembly comprising a housing structure and a first transducer and a second transducer arranged in said housing structure is disclosed. The ear probe assembly further comprising a channel structure comprising at least a first transducer entrance and a second transducer entrance configured to receive first and second sound ports of the transducers, where further a tip portion is configured to engage with the channel structure in a detachable manner.

15 Claims, 4 Drawing Sheets

(56) References Cited

U.S. PATENT DOCUMENTS

2016/0183850 A1 6/2016 Geertsen
2016/0324478 A1 11/2016 Goldstein

EAR PROBE FOR HEARING TESTING

This application is a Continuation of copending application Ser. No. 15/840,299, filed on Dec. 13, 2017, which claims priority under 35 U.S.C. § 119(a) to Application No. 16204046.3, filed in Europe on Dec. 14, 2016, all of which are hereby expressly incorporated by reference into the present application.

FIELD

The present disclosure relates to a diagnostic device for testing the functionality of the auditory system of a patient. More particularly, the disclosure relates to an improved ear probe configuration of the diagnostic device.

BACKGROUND

Within hearing diagnostics, it is of great importance to be able to perform efficient and accurate hearing test of infants as well as adults. When assessing the hearing loss of humans, a hearing diagnostic device, which is configured to be controlled to emit a sound signal and collect a response from the auditory system of the patient, is generally used. Different diagnostic devices, which are used for different hearing testing purposes, exist.

Diagnosing hearing impairment in the auditory system of infants or adults by use of e.g. Optoacoustic Emissions (OAE's), Auditory Evoked potentials (AEP), Acoustic Reflectivity (AR), Optoacoustic Reflectance (OR) or Tympanometry often requires inserting an acoustic probe into the ear canal of a patient. Typically, such acoustic probes consist of at least one transducer, and sometimes two transducers, configured for generating and emitting a stimulus signal to the auditory system of the patient. The auditory system of a human may respond to the stimuli signal by reflecting an emission signal, and during OAE measurements this emission signal is measured by a third transducer of the acoustic probe. The emission signals measured are easily affected by noise introduced into the signal, therefore an acoustic probe which accurately transmits and records the signal and which limits noise introduced into the measurements, is preferable.

Current hearing diagnostic devices continuously aim at optimizing the design in order to limit especially noise introduced into the measurements. Usually the acoustic probes are connected to a handheld device either directly by forming an integrated part of the handheld device or connected to the handheld device by a cable, which cable in one end is connected to the handheld device and in the other end is connected to the acoustic probe. However, several drawbacks exist for both types of devices, which therefore need further improvements to optimize the hearing diagnostic measurement setup.

A handheld device having the acoustic probe substantially integrated into the device has been extensively used and developed to optimize the accuracy of the diagnostic measurements. However, with a handheld device there still exist the risk of introducing errors into the measurement, since a handheld device is placed directly against the patient's ear, and any movement of the handheld device while the acoustic probe is inserted into the ear increases the risk of introducing noise. A similar risk of introducing noise is present in the cable attached acoustic probe solutions, where a movement of the cable to adjust the acoustic ear probe introduces noise and instability of the transducer, which is why a proper placement of the ear probe against the ear canal is needed in order to limit the risk of introducing noise.

Furthermore, when performing diagnostic hearing measurements, the risk of cross-contamination between two patients if the device is not sufficiently cleaned after use is increased when using a handheld device. That is, a large part of the handheld device comes into contact with the skin of a patient during measurement, and therefore needs substantive cleaning after a diagnostic hearing test has been performed. In a cable attached acoustic probe solution, such cross-contamination may be limited due to the cable creating a distance between the patient and the handheld part of the device. However, such cable solutions requires a secure coupling to the ear canal, since any movement of the cable during measurement may introduced unwanted noise.

The risk of erroneous measurements is further increased when debris is allowed to enter the acoustic tubes of the acoustic ear probe. Debris, which is allowed to enter and get trapped in the acoustic tubes may block the acoustic path which influences the calibration parameters of the probe and the subsequent diagnostic measurements.

In addition, during a diagnostic hearing measurement, especially when testing infants, the space available to operate a handheld device is limited. That is, when testing e.g. an infant, the infant usually lies in the arms of a parent or a crib, and the operator needs to operate the device in a limited amount of space, which may be difficult with a large handheld device, which should be arranged closely to the ear of the infant. Therefore, a repositioning of the handheld device and the ear probe may be necessary prior to the measurements, which increases the risk of disturbing the infant and introducing noise into the subsequent measurement. Furthermore, with a handheld device having an integrated ear probe, the operator should keep the handheld device in place, while the operator at the same time should angle the device such that the measurement screen is visible.

Thus, the drawbacks of a handheld devices having an integrated acoustic ear probe or a cable attached acoustic ear probe are many, and a need therefore exists to provide a solution, which limits at least some of these drawbacks to provide an improved diagnostic device that provides more accurate measurements and a more efficient diagnostic environment setup. Therefore, there is a need to provide a solution that addresses at least some of the above-mentioned problems. The present disclosure provides at least an alternative to the prior art solutions.

SUMMARY

This and further objectives are met by an ear probe assembly comprising a housing structure having a proximal side and a distal side, wherein at least a first transducer and a second transducer are arranged in the housing structure. The first transducer comprising a first sound port and the second transducer comprising a second sound port. The ear probe assembly furthermore comprises at least one channel structure comprising at least a first transducer entrance and a second transducer entrance, configured to receive the first and second sound ports, respectively, wherein the channel structure protrudes from the proximal side of the housing structure. For guiding sound emitted by at least one of the transducers to the ear canal of a patient, the at least one channel structure forms an acoustic path between the first and second transducer and a tip portion of the ear probe assembly, where the tip portion is configured to connect with the channel structure. The tip portion furthermore comprises a set of integrated acoustic channels, which set of integrated acoustic channels are configured to connect with the channel structure in a detachable manner.

Accordingly, an ear probe, which comprises a detachable tip portion having a set of integrated acoustic channels, which are acoustically sealed and connected with the channel structure, is provided. This allows for an efficient ear probe of e.g. a diagnostic device, which limits noise and efficiently seals the acoustic path between the at least one or more transducers and the tip portion, thereby optimizing the acoustic signal emitted by the transducer and the further measurements by another transducer of a signal emitted by the auditory system of a patient.

In diagnostic devices used for hearing impairment testing, it is especially important to avoid cross-talk components introduced during the measurement, since the signals emitted by the auditory system as a response to a stimulus, are small and easily contaminated by cross-talk from the electronics of the measurement device. Thus, to reduce potential cross-talk in the acoustic probe of the diagnostic device, the ear probe assembly may in one embodiment be configured such that the first transducer comprises a first membrane and the second transducer comprises a second membrane, wherein the first and second transducers are arranged in the housing structure, such that the first membrane lies substantially perpendicular to the second membrane. Such an arrangement of the first and second transducer decreases the mechanical cross-talk in the ear probe assembly. That is, the signal produced by the second transducer (e.g. a receiver) may induce a signal (due to mechanical vibration of the receiver) in the first transducer, where the first transducer may be a measurement transducer (e.g. a microphone). Any cross-talk from the second transducer to the first transducer (i.e. a measurement transducer) may introduce an unwanted signal component in the hearing measurements performed by the hearing diagnostic device.

Furthermore, the perpendicular arrangement of the membrane of the first transducer and the membrane of the second transducer also provides and optimized space consumption within the housing structure of the ear probe assembly. With such construction, the first and second transducer can be arranged so that a limited amount of space is needed and a smaller housing structure is achieved.

Accordingly, in an embodiment of the ear probe assembly the housing structure may comprise a top end and a bottom end defining a longitudinal axis of the housing structure. Furthermore, the second transducer may comprise a top end facing the top end of the housing and a bottom end facing the bottom end of the housing. The first transducer may comprise a proximal side and a distal side facing the proximal side and the distal side of the housing structure, respectively, and defining a longitudinal axis of the sound port of the first transducer, where the longitudinal axis of the sound port is arranged substantially perpendicular to the longitudinal axis of the housing structure. Thus, the first and second transducer are arranged in relation to each other such that a bottom side of the first transducer faces the top end of the second transducer and a top side of the first transducer faces the top end of the housing structure. This allows for a better sound performance in the ear probe, where less cross-talk is introduced from e.g. mechanical vibrations between the first and second transducer. Furthermore, less space in the housing structure is needed to contain the first and second transducer, which in effect provides the possibility of a smaller housing structure of the ear probe assembly that is easier to handle for an operator handling the diagnostic device.

Furthermore, in an embodiment, a distal end of the first transducer is arranged to be substantially flush with a distal side of the second transducer. Having the first and second transducer substantially flush with each allows for a substantially flat surface area on at least a distal side of the housing structure, in a space optimized solution.

In a further embodiment, a circuitry board, such as a printed circuitry board (PCB), of the housing structure is arranged so as to cover the first transducer and the second transducer. This allows for a simple assembly process of the ear probe assembly, where the risk of overheating and damaging of the transducers during soldering of electrical components to the PCB is reduced. Furthermore, by attaching a PCB directly on the transducers the first and second transducer may be easily assembled prior to connection with the remaining components of the ear probe assembly.

Accordingly, in one embodiment, the first and second transducers are assembled together with the PCB and the channel structure. This combined structure is, after assembly, "clicked" into engagement with the housing structure, followed by a soldering of electrical components, such as wires to the PCB. Consequently, the components may be secured tightly in the housing by use of glue or other suitable means, such as a by mechanical fixation by adding attaching elements and/or structure to the PCB and the components, which are to be secured to the PCB.

In more detail, the circuitry board may in one embodiment, be arranged such that in a top end of the housing structure the circuitry board is connected to a distal end of the first transducer. From here, the circuitry board may extend along the longitudinal direction of the housing to a bottom end of the second transducer, where the circuitry in the bottom end is connected to the second transducer. This allows the circuitry board to follow the outer contours of the transducers, whereby space is optimized.

With the transducer arrangements in the housing structure of the ear probe assembly as described herein, a substantially longitudinal housing structure having a protruding channel structure is provided for. The substantially longitudinal housing structure allows for a better alignment of the tip portion to the ear canal of the user, since a small housing structure at least in the "width direction" defined by the direction between the proximal side of the housing structure and the distal side of the housing structure creates a small moment arm, which stabilizes the housing structure when the tip portion is inserted into the ear canal of a patient.

That is, in an embodiment, the housing structure may comprise a substantially flat surface area on the proximal side, wherein a distal side of the tip portion is configured to abut the substantially flat surface. Furthermore, the channel structure of said housing structure may extend into the acoustic channels of the tip portion, such that at least a part of the channel structure is substantially contained in the tip portion. This allows for an efficient seal between the tip portion and the channel structure, while also providing a substantially stable tip portion, which does not easily bend when the tip portion is arranged in the ear canal of a patient.

Furthermore, this also allows for a better ear probe placement in the ear in such a way that the operator does not need to stabilize the probe by holding the probe cable, which would cause noise to be induced into the measurements.

In more detail, in an embodiment, the ear probe assembly may be configured such that a distance between a proximal surface and a distal surface of the tip portion defines a length of the tip portion, wherein the channel structure is extending into the tip portion so as to take up at least half of the length of said tip portion. This allows for a substantially changing stability of the tip portion along the length thereof, such that the tip portion is more stable at the distal surface where the tip portion abuts the housing structure and less stable (i.e. more flexible) along the length of the tip portion towards the proximal side thereof.

When attaching a tip portion of the acoustic ear probe to the acoustic channels of the transducers, a correct alignment of the acoustic channels of the tip portion with the acoustic channels of the transducer should be achieved. This complexity of alignment between the tip portion and the channel structure of the ear probe assembly is alleviated with an ear probe assembly, which in one embodiment is configured such that the channel structure is formed with a substantially triangular circumference. The tip portion comprises a corresponding triangular opening configured to engage said triangular circumference of said channel structure in a detachable manner. This allows an attachment structure of the ear probe assembly, which can be attached in a one-way manner, in that the triangular shape allows for a perfect alignment between the acoustic channels of the tip portion and the acoustic path of the channel structure.

Furthermore, in an embodiment, the channel structure comprises at least two, preferably three independent and acoustically separated acoustic paths, which acoustic paths are each configured to connect with at least two, preferably three independent and acoustically separated acoustic channels of the tip portion.

In an embodiment, the channel structure may comprise at least three channels, wherein each channel comprises one of the transducer entrances, each configured to receive a corresponding acoustic channel of the tip portion in a proximal end thereof, and configured to receive the first and second sound ports of said first and second transducers in a distal end of said channel structure, wherein a filter is arranged in each of said three channels of said channel structure. This allows a sufficient damping of the impulse response of the ear probe.

In one embodiment, the filter may be a wax filter, which is configured to be exchangeable, inserted into each of the three channels of the channel structure. This allows for a disposable wax guard, which may easily be replaced by the user. Accordingly, not only does the tip portion reduce wax from entering the sound ports of the transducer, but also the wax guard of the channel structure provides an extra protection. Thus, if wax does penetrate into the channel structure, this may be stopped by the wax guard prior from entering the sound ports of the transducers.

The embodiments described herein, may furthermore comprise both an acoustic filter and a wax filter, where the wax filter ensures that debris is kept out of the acoustic channels of the channel structure to improve the acoustics of the probe, and where the acoustic filter improves the impulse response characteristics of the acoustic ear probe. The acoustic filters act as resistors to damp resonances in the frequency response of the transducers of the acoustic ear probe and thereby the length of the impulse responses. In certain measurements, such as e.g. Transiently evoked optoacoustic emissions (TEOAE), it is assumed that the impulse response of the acoustic ear probe has completely decayed after 2.5-4 ms in order to distinguish between speaker artefacts and an actual OAE response and if no filter is present, this would not be the case and the measurement would have a false response. Accordingly, the acoustic filters improve the accuracy of the acoustic probe measurements, by damping the resonances in the frequency response of the transducers.

In an embodiment, which is to be explained in further detail later, the channel structure may comprise a first and/or a second engagement structure, which is configured to engage with a part of said housing and/or the tip portion to provide an efficient seal and locking between the elements of the ear probe assembly.

It should be noted that, in an embodiment, the first transducer is preferably a receiver configured to emit a stimuli and the second transducer is a microphone configured to record an emitted signal from the auditory system being tested.

In accordance with embodiments described herein, the ear probe is configured to transmit an acoustic signal through one of the acoustic channels of the ear tip and to receive an acoustic signal through one of said acoustic channels and emitted by an auditory system of the person under test. Accordingly, as previously described, the acoustic channel of the channel structure and the ear tip are configured to as to be acoustically separated from each other.

Furthermore, in one embodiment, the bottom end of the housing structure is preferably connected to a cable, where the cable is another end is connected to a hearing testing system configured to control a hearing test setup. Accordingly, the diagnostic hearing testing system according to embodiments herein should preferably be understood so as to comprise a handheld device, from where a cable extends in order to optimize the hearing test measurements. By such a device, substantially constructed according to the embodiments described herein, a diagnostic device, which substantially overcomes the drawbacks of the prior art is provided for.

BRIEF DESCRIPTION OF DRAWINGS

The aspects of the disclosure may be best understood from the following detailed description taken in conjunction with the accompanying figures. The figures are schematic and simplified for clarity, and they just show details to improve the understanding of the claims, while other details are left out. Throughout, the same reference numerals are used for identical or corresponding parts. The individual features of each embodiment may each be combined with any or all features of the other aspects or embodiment. These and other aspects, features and/or technical effect will be apparent from and elucidated with reference to the illustrations described hereinafter in which:

DETAILED DESCRIPTION

The detailed description set forth below in connection with the appended drawings is intended as a description of various configurations. The detailed description includes specific details for the purpose of providing a thorough understanding of various concepts. However, it will be apparent to those skilled in the art that these concepts may be practiced without these specific details. Several aspects of the device and methods are described by various structures, functional units, modules, components, circuits, steps etc. (collectively referred to as "elements"). Depending upon the particular application, design constraints or other reasons, these elements may be implemented using electronic hardware, computer program, or any combination thereof.

A diagnostic device used for testing hearing impairment generally includes a handheld device and or a stationary device, to which an acoustic probe (i.e. an ear probe) is connected through e.g. a cable or integrated into e.g. the handheld device. The stationary device or handheld device comprises electronics configured to generate a stimuli signal to the acoustic ear probe, such that a stimuli signal may be transmitted into the ear canal of a patient by use of the transducers of the acoustic ear probe. Furthermore, the handheld or stationary device may comprise a processing unit configured to process a received signal, measured from the auditory system of a patient, by a second transducer of the acoustic ear probe. The processing unit may be configured to process the signal to obtain a hearing impairment characteristic of the patient being examined. Furthermore, the handheld or stationary device may comprise a display, from where an operator of the device may activate the device to send out a stimuli signal, analyze the signal measured by a measurement transducer of the acoustic ear probe etc.

It should be noted that throughout the disclosure, the wording "proximal" should be understood as defining a side of an element (e.g. tip portion, housing structure, transducers etc.) facing the opening of the ear canal of a patient, when the ear probe assembly is operated in the measurement position. Accordingly, the wording "distal" should be understood as a side opposite to the proximal side of and facing away from the opening into the ear canal of a patient.

Figure 1:
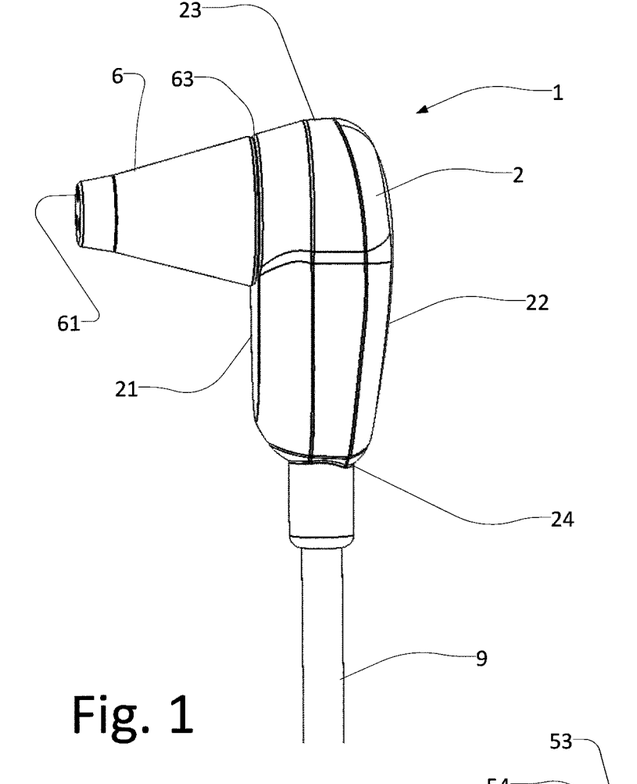
FIG. 1 illustrates an ear probe assembly according to an embodiment of the disclosure.

Referring initially to FIG. 1, a general overview of an ear probe assembly according to the disclosure is illustrated. The ear probe assembly 1 comprises a housing structure 2 having a proximal side 21 and a distal side 22. The housing structure 2 is configured to contain at least a first transducer and a second transducer, where the first transducer comprises a first sound port and the second transducer comprising a second sound port (not shown). Furthermore, the ear probe assembly 1 comprises a tip portion 6, which further comprises a set of integrated acoustic channels 61. The tip portion 6 is configured to engage with a channel structure (not shown) of the ear probe assembly 1 in a detachable manner. The tip portion 6 is configured to engagement with the channel structure, such that a side portion 63 (i.e. the distal side) of the tip portion abuts a part of the proximal side 21 of the housing structure.

The housing structure is furthermore in a bottom end 24 connected to a cable 9, which in the opposite end connects to e.g. a handheld device configured to be operated to control a measurement of the hearing impairment measurement setup in accordance with the definitions provided herein. It should be noted that even though not illustrated in more detail, the probe tip is configured such that the probe tip 6 substantially contains the channel structure, such that a sufficient acoustic seal is obtained. Furthermore, the detachable probe tip 6 makes it easy to change from patient to patient upon performing hearing measurements, whereby cross-contamination and clogged ear tips are avoided.

Accordingly, the ear probe assembly according to the disclosure is configured to transmit an acoustic signal through one of the acoustic channels of the ear tip 6 and to receive an acoustic signal emitted by an auditory system of a patient through one of the acoustic channels.

In the following figures, embodiments of the ear probe assembly will be described in more detail. It should be noted that substantially same elements will be provided with the same numbering.

Figure 2:
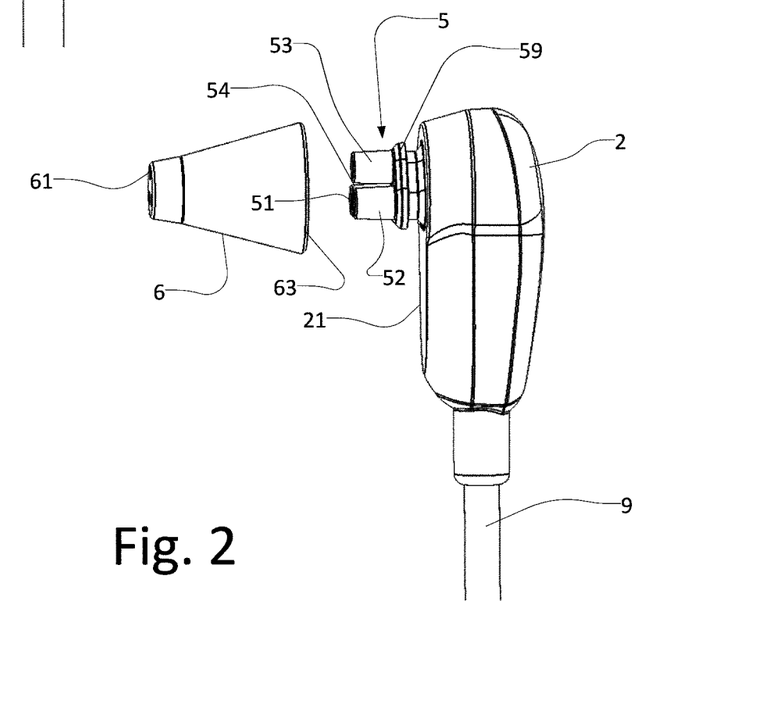
FIG. 2 illustrates a partly exploded side view of an ear probe assembly according to FIG. 1.

Referring now to FIG. 2, a partly exploded view of the ear probe assembly 1 according to FIG. 1, where the tip portion 6 has been detached from a part of the housing structure 2, is illustrated. In more detail, FIG. 2 illustrates a channel structure 5, which forms part of the housing structure 2. That is, in the embodiment shown, at least one channel structure 5 is configured to protrude from the proximal side 21 of the housing structure 2. The channel structure 5 comprises at least a first transducer entrance and a second transducer entrance, configured to receive a first and second sound port of the first and second transducer in the housing structure, explained in further details in the following. The at least one channel structure 5 forms an acoustic path 51 from the first and second transducer to the tip portion 6. The ear probe is configured to connect with the channel structure 5, such that the set of integrated acoustic channels 61 connects with the channel structure 5.

As may be best seen in at least FIG. 1, the housing structure 2 comprises a substantially flat surface area on the proximal side 21, wherein a distal side 63 of the tip portion 6 is configured to abut the substantially flat surface forming the proximal side 21 of the housing structure.

As seen in FIG. 2, the channel structure 5 may comprise at least three channels 52, 53, 54, wherein each channel 52, 53, 54 is configured to receive a sound port of either the first transducer or the second transducer in the distal end thereof, and in the opposite proximal end configured to connect with a corresponding acoustic channel 61 of the tip portion 6. Accordingly, the channels 52, 53, 54 are configured to be contained in the integrated acoustic channels 61 of the tip portion, whereby a sealed acoustic path between the transducers of the housing structure and the ear canal of a patient is established.

Furthermore, as seen on FIG. 2, the channel 5 structure further comprises an engagement structure 59 (also denoted a second engagement structure), which is configured to engage with the tip portion 6.

With the construction ear probe assembly having the channel structure 5 and tip portion 6 as described herein, not only an efficient acoustic seal is achieved but also a sufficiently stable ear probe assembly. That is, the channel structure being substantially contained in the tip portion allows a proper alignment with the ear, since the "moment arm" of the probe tip in relation to the housing structure is minimized (to be explained in further detail). Accordingly, the risk of an unintentional bending by e.g. up and/or down movement of the ear probe causing noise, when the probe is inserted into the ear is decreased.

Figure 3:
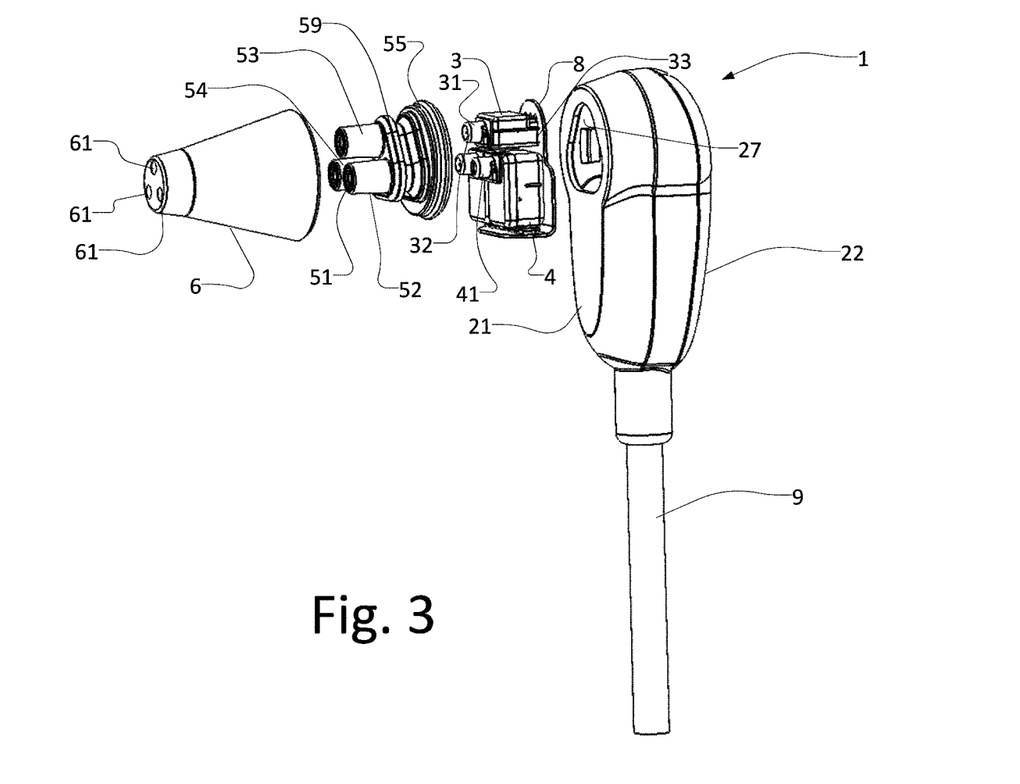
FIG. 3 illustrates an exploded perspective view of an ear probe according to an embodiment.

The ear probe according to embodiments of the disclosure is illustrated in more detail in FIG. 3, which shows an exploded view of the ear probe assembly 1. As seen in FIG. 3, the ear probe assembly comprises at least a first transducer 3 and a second transducer 4, which are arranged in the housing structure 2. Preferably, a third transducer 7 is also arranged in connection with the first 3 and second transducers 4. The arrangement of the transducers 3, 4, 7 is best illustrated in FIGS. 4 and 5 and will be explained in further detail in relation to these figures.

FIG. 3 furthermore illustrates the channel structure 5, which comprises at least two, preferably three independent and acoustically separated channels 52, 53, 54, defining an acoustic path on the interior sides thereof. The acoustic paths are each configured to connect with the at least two, preferably three independent and acoustically separated acoustic channels 61 of the tip portion. The acoustic channels 61 of the tip portion 6 is in FIG. 3 illustrated with the acoustic channels 61 opening into a proximal side of the tip portion 6. At the distal side of the ear tip 6, the acoustic channels forms openings configured to receive the acoustic separated channels 52, 53, 54 of the channels structure 5.

Figure 4:
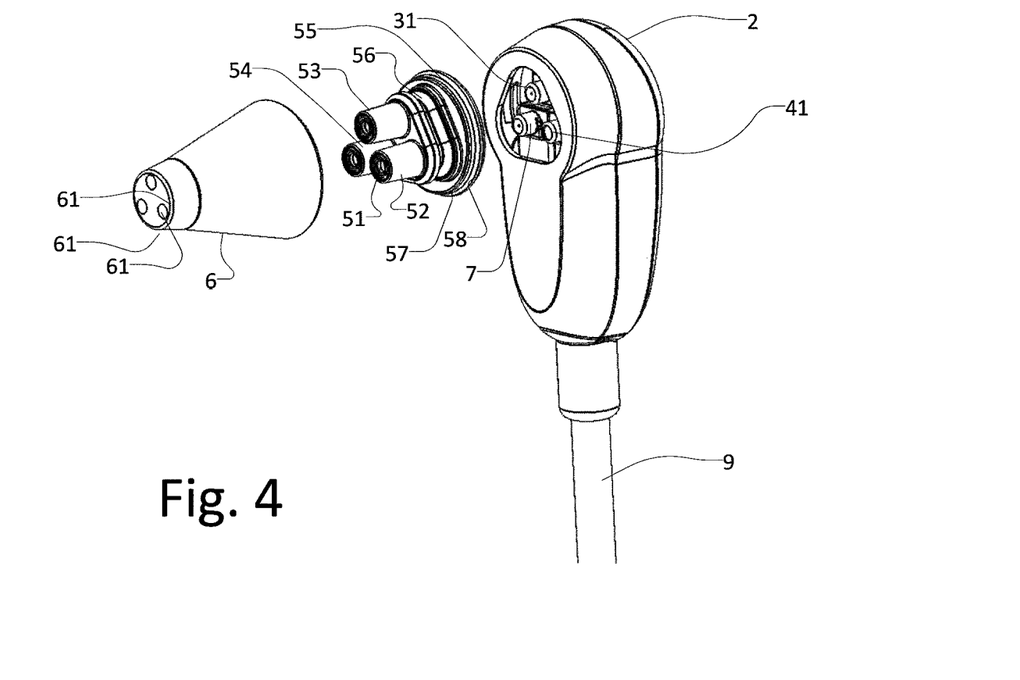
FIG. 4 illustrates a partly exploded perspective view of an ear probe according to an embodiment, where the transducer assembly is mounted in a housing structure.

Furthermore, FIGS. 3 and 4 illustrate the channel structure 5 according to embodiments of the disclosure in more detail. As is seen, the channel structure 5 comprises a first engagement structure 55 configured to engage with a part of the housing structure 2 on an inner side 27 of the housing structure to lock the channel structure 5 in said housing structure 2.

Figure 5:
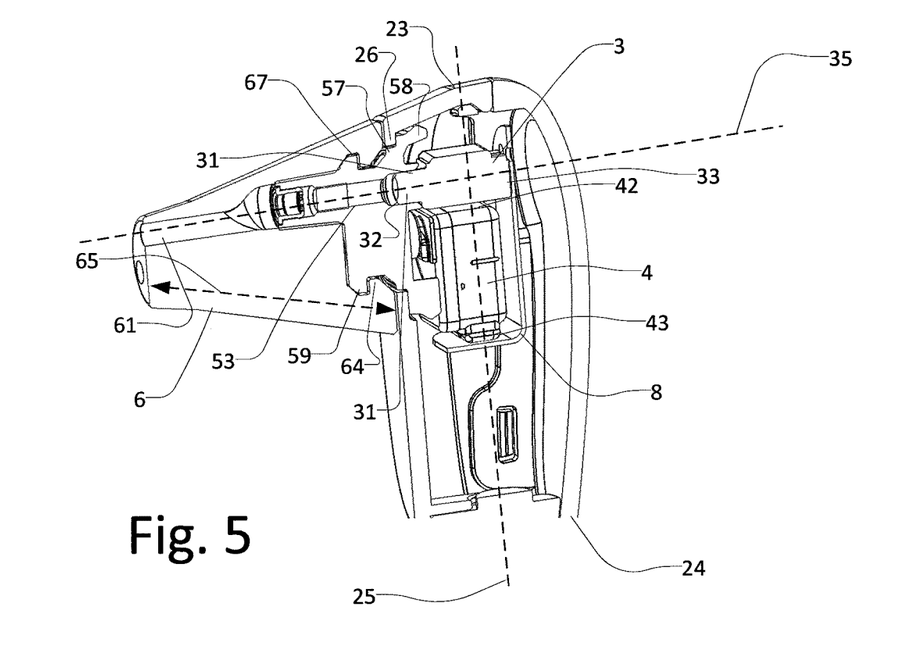
FIG. 5 illustrates a cross-sectional side view of an ear probe assembly according to an embodiment of the disclosure.
Figure 6:
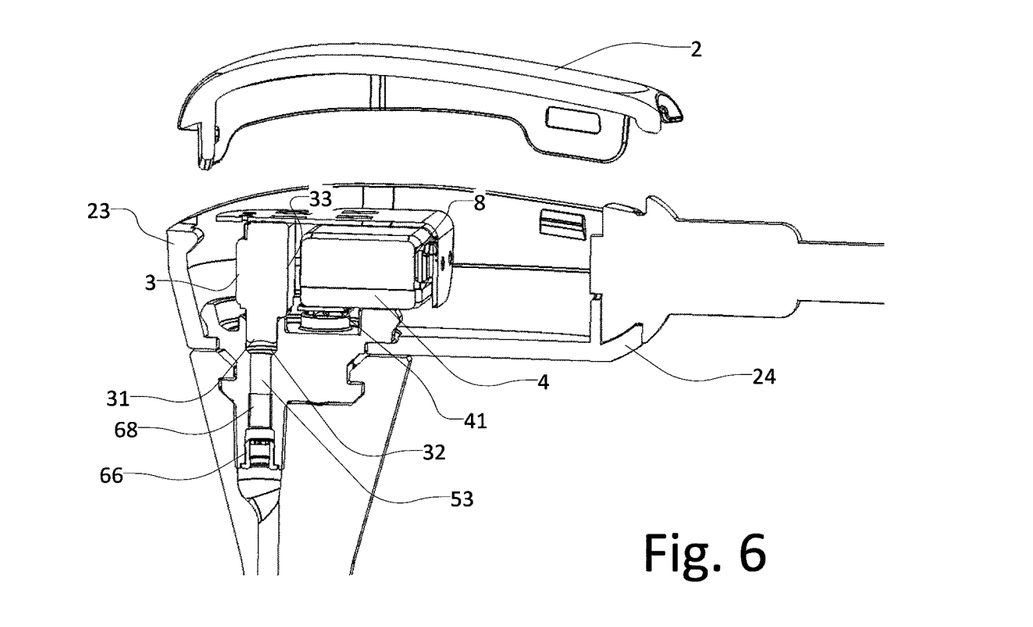
FIG. 6 illustrates a partly exploded view of the ear probe assembly according to an embodiment of the disclosure, wherein the circuitry is seen in more detail.

In more detail, and best illustrated in further details in FIGS. 5 and 6, the first engagement structure 55 of the channel structure 5 comprise a step-wise flange structure protruding from a base portion 56 of the channel structure 5. In other words the base portion 56 of the channel structure 5 forms a substantially triangular base (see e.g. FIG. 4) of the channel structure 5. From the distal side, a protrusion is formed, which form a first step 57 having a first diameter and which continues into a second step 58 with a second larger diameter than the first step. As best seen in FIG. 5, the transition between the first step 57 and the second step 58 of the plate shaped flange protrusion forming the first engagement member 55 is configured to be recessed in the housing structure 2, such that the second step 58 abut a protrusion 26 in the housing structure 2, whereby the first engagement member 55 is retained inside the housing structure upon assembly thereof.

Accordingly, the channel structure 5 may as illustrated be formed with a substantially triangular circumference, wherein the tip portion 6 comprises a corresponding triangular opening configured to engage the triangular circumference of the channel structure 5 in a detachable manner. In this way, a "one-fit" attachment is achieved. That is, the substantially triangular shaping of the channel structure 5 and the tip portion 6 allows an easy alignment of the acoustic channels 61 of the tip portion and the channels 52, 53, 54 of the channel structure 5.

In a further embodiment, also illustrated in FIG. 3, the channel structure 5 comprises a second engagement structure 59, which second engagement structure is configured to engage with the tip portion 6. Accordingly and with reference to e.g. FIGS. 5 and 6, the second engagement structure 59 is formed as a protruding flange extending as a circular protrusion from said channel structure 5. The second engagement structure 59 is configured to engage with a groove 67 of the tip portion 6. Furthermore, a space between the second engagement structure 59 and the first step 57 of the first engagement structure 55 is configured to receive a protrusion 64 of the tip portion. Accordingly, the first and second engagement structures of the ear probe assembly ensures that the channel structure is tightly connected to the housing structure and furthermore that the ear tip is tightly connected to the ear tip.

Returning now to FIGS. 5 and 6, the transducer assembly will be explained in more detail. As previously mentioned, the ear probe assembly 1 comprises at least two transducers 3, 4 where the first transducer 3 comprises a first membrane (not shown) and the second transducer 4 comprises a second membrane (not shown). In order to reduce cross-talk between the transducers 3, 4, the first 3 and second 4 transducers are arranged in the housing structure 2, such that the first membrane of the first transducer 3 lies substantially perpendicular to the second membrane of the second transducer 4. That is, the first membrane of the first transducer 3 substantially follows the longitudinal axis 35 of the first transducer defined by the longitudinal axis of the first sound port 31 of the first transducer 4, whereas the second membrane of the second transducer 4 substantially follows a longitudinal axis 25 of the housing structure 2. In this way, the first and second membrane are arranged perpendicularly to each, which at least reduces the mechanical cross-talk between the transducers.

In more detail in an embodiment, the housing structure comprises a top end 23 and a bottom end 24 defining said longitudinal axis 25 of the housing structure. The second transducer 4 comprises a top end 42 facing the top end 23 of the housing structure 2 and a bottom end 43 facing the bottom end 24 of the housing structure 2. Furthermore, the first transducer 3 comprises a proximal side 32 and a distal side 33 facing the proximal side 21 and the distal side 22 of the housing structure 2, respectively. The proximal side 32 and the distal side 33 of the first transducer defines said longitudinal axis 35 of the first sound port 31 of the first transducer 3. Thus, the longitudinal axis 35 of said first sound port 31 is substantially perpendicular to the longitudinal axis 25 of the housing structure. Furthermore, the transducers 3, 4 are arranged such that a bottom side of the first transducer faces the top end of the second transducer and a top side of the first transducer faces the top end of the housing structure.

With the arrangement of the transducer as described herein, not only is cross-talk between the transducer is minimized, but also a space optimization is achieved. That is, when arranging the transducer as previously described a substantially flat transducer arrangement may be obtained. That is, a smaller width of the housing is achieved, allowing for a more stable ear probe assembly which is more easily aligned with the ear of a patient.

Accordingly, in a further development of this embodiment, a distal end of the first transducer is arranged to be substantially flush with a distal side of the second transducer. This creates a substantially flat surface area of the transducer assembly, whereby less space is needed for the transducers to be arranged in the ear probe housing structure 2.

Figures 7, 8:
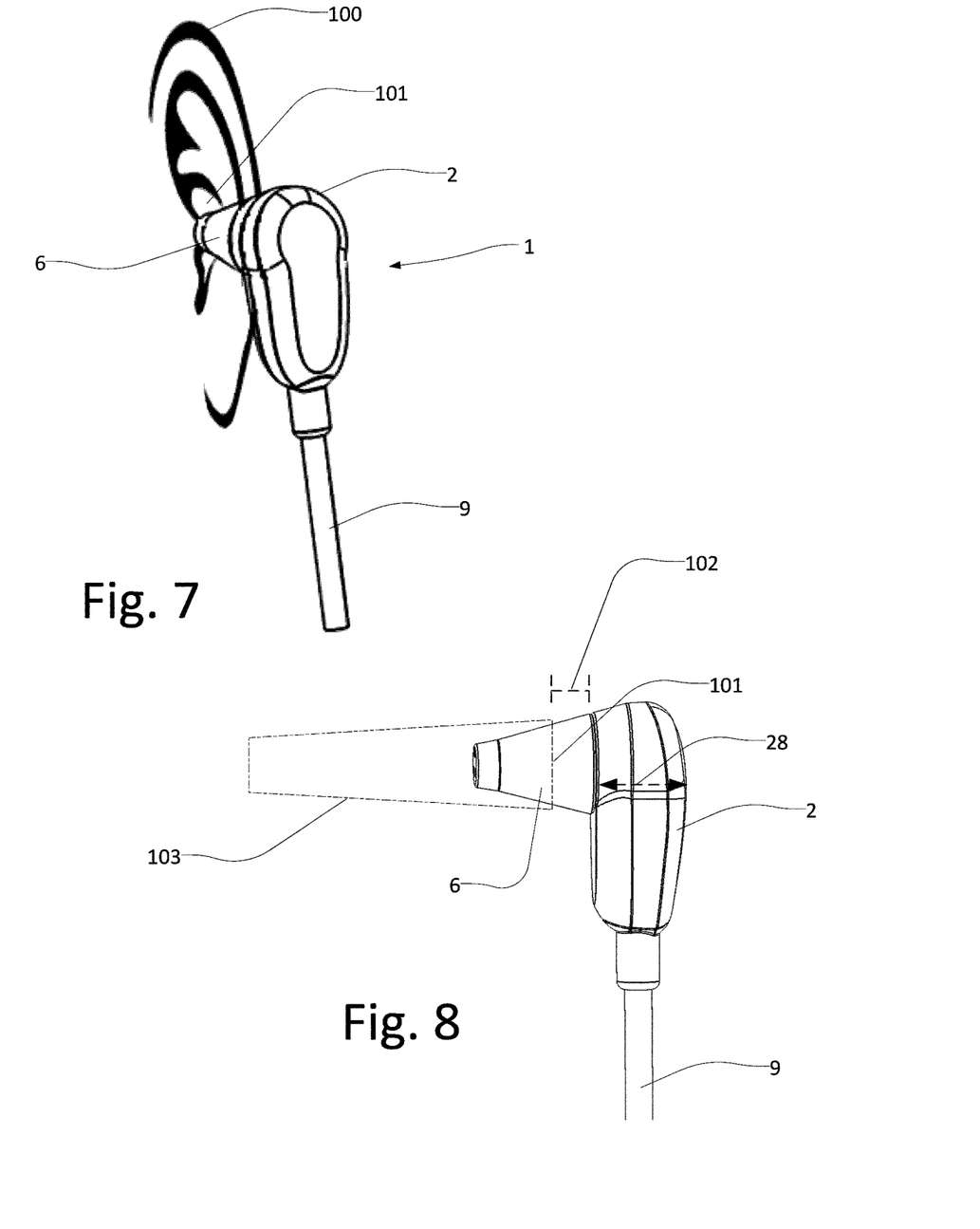
FIG. 7 illustrates an insertion of the ear probe assembly arranged in proximity to an ear of a patient.
FIG. 8 illustrates a schematic cross-section of an ear canal having the ear probe assembly inserted therein.

Accordingly, the width, indicated in FIG. 8 as the dotted line 28, of the housing structure 2, defined by the distance between the proximal side 21 and the distal side 22 of the housing structure 2 may be decreased due to this substantially "flat" transducer assembly. As illustrated in e.g. FIGS. 5 and 6, the ear probe assembly is configured such that a distance between a proximal surface and a distal surface of the tip portion defines a length (illustrated by the dotted line 65) of the tip portion 6. As illustrated, the channel structure 5 is at least in one embodiment extending into the tip portion 6 so as to take up at least half of the length of the tip portion 6. However, it should be noted that the channel structure may extend more or less into the tip portion 6. By providing the channel structure 5 such that it substantially extends into the tip portion, a better probe placement is allowed for in the ear, since the moment arm of the tip portion is decreased. In this way the operator of the diagnostic device does not need to stabilize the ear probe by holding the probe cable, whereby noise is reduced.

In a further embodiment, best illustrated in FIG. 6, the ear probe assembly comprises a circuitry board 8, which is arranged in the housing structure 2 so as to substantially cover the first transducer 3 and the second transducer 4.

In further details, in an embodiment, the circuitry board 8 is arranged in the housing structure 2, such that in a top end 23 of the housing structure 2, the circuitry board is connected to a distal end of the first transducer 3. From here, the circuitry board 8 extends along the longitudinal direction of the housing structure 2 to a bottom end 43 of the second transducer 4. In this bottom end 43 the circuitry board 8 is connected to the second transducer 4.

Arranging the PCB in connection with the transducers as described, provides for a simplified assembly process, where the PCB is mounted to the transducers prior to insertion in to the housing structure. Furthermore, the risk of overheating and damaging the transducers during soldering is reduced.

In an embodiment best illustrated in e.g. FIGS. 5 and 6, the ear probe assembly 1 is as previously described configured to receive the first sound port 31 and second sound port 41 of the first 3 and second 4 transducers in a distal end of the channel structure. In the embodiment shown in FIG. 5, a filter 66 is arranged in a channel 53 of the channel structure 5. Even though not shown in more detail in this cross-sectional view of the ear probe assembly, each of the three channels 52, 53, 54 of the channel structure 5 may have a filter 66 arranged therein. It should be noted that the ear probe assembly could be made without this filter. However, for example, the filter could be construed as a wax filter which prohibits wax from entering into the transducers of the ear probe assembly.

Furthermore, with e.g. reference FIG. 6, the acoustic ear probe may comprise both an acoustic filter 68 and a wax filter 66, where the wax filter ensures that debris is kept out of the acoustic channels of the channel structure to improve the acoustics of the probe, and where the acoustic filter improves the impulse response characteristics of the acoustic ear probe. The acoustic filters act as resistors to damp resonances in the frequency response of the transducers of the acoustic ear probe and thereby the length of the impulse responses. Accordingly, the acoustic filters improve the accuracy of the acoustic probe measurements, by damping the resonances in the frequency response of the transducers.

Referring now to FIGS. 7 and 8, the substantially combined structural advantages of the ear probe assembly according to embodiments described herein will be explained in view of a diagnostic setup. The ear probe assembly 1 is configured to be inserted into e.g. an adult or infant ear 100 of a patient and of which patient the functionality of the auditory system should be measured. The tip portion 6 of the ear probe assembly 1 is inserted into the ear canal 103 of the patient, and the housing structure 2 is substantially aligned with the outer contours 101 of the ear. Accordingly, the ear probe assembly 1 is constructed such that the housing structure 2 comprises a substantially flat surface area, which aligns with the outer contours of the ear, whereby a secure and stable alignment with the ear reducing the risk of introducing noise due to re-positioning of the ear probe is achieved.

This is substantially achieved by the ear probe assembly construction described herein, which provides a reduced moment arm 102 of the ear. That is, the length 102 (i.e. the moment arm) of the tip portion 6 which extends outside the ear canal, when the tip portion 6 is inserted into the ear canal 103 is minimized due to the arrangement of the channel structure 5 in the tip portion 6 as described herein. Furthermore, the tip portion is stable and not easily "bendable", which together with the construction of the housing limits the need for re-positioning and thereby limits the introduction of noise.

It should be noted that the first transducer of the ear probe assembly preferably is a microphone, and the second and third transducers preferably are configured as receiver. The microphone is intended for measuring an acoustic response of the auditory system, which response is triggered by an emitted signal introduced into the ear canal by use of the one or more receivers.

With reference to at least FIGS. 3 and 6, a method of assembly of the ear probe assembly according to embodiments of the disclosures will be explained. As described previously, the ear probe assembly at a top level comprises a tip portion 6 connected to a channel structure 5 protruding from a housing structure 2. Upon assembly of the ear probe assembly a first step is to provide a housing structure having an opening, into which the channel structure 5 should be arranged. A second step includes providing the above mentioned channel structure 5, and a set of transducers. In a first step of assembly, at least a first and a second transducer is connected with the channel structure. In a second step of assembly, a printed circuit board is attached to the transducers, such that a probe assembly comprises the channel structure 5, the first and second transducers and a PCB is provided. Accordingly, in a third step of assembly, the channel structure 5, with the PCB and transducer set attached thereto is arranged in a first shell part of the housing structure 2. The first shell part comprises the opening, through which the channel structure 5 protrudes. Furthermore, the first shell part of the housing structure 2 also comprises the protrusion 26 (c.f FIG. 5), which is configured to retain the first engagement member 55 of the channel structure 5 in the housing. In a fourth step of assembly, the cable 9, which in one end is configured to connect with the housing structure 2, and in the other end to diagnostic handheld operative device, is connected to the housing structure and the electrical wires configured to control the transducers of the housing structure 2 is soldered on the back of the PCB. Consequently, in a final step, the interior of the housing structure is filled with a glue to secure the different components in the housing structure 2, and a second shell structure (formed as a lid) is attached to the first shell structure of the housing 2. Preferably, the second shell structure is snapped into engagement with the first shell structure.

With the method described herein, especially with the subassembly of the PCB and transducers improves the assembly process and decreases assembly cost, since the transducers together with the PCB and the channel structure in this way are easily and accurately arranged in the housing.

It is intended that the structural features of the devices described above, either in the detailed description and/or in the claims, may be combined with steps of the method, when appropriately substituted by a corresponding process.

As used, the singular forms "a," "an," and "the" are intended to include the plural forms as well (i.e. to have the meaning "at least one"), unless expressly stated otherwise. It will be further understood that the terms "includes," "comprises," "including," and/or "comprising," when used in this specification, specify the presence of stated features, integers, steps, operations, elements, and/or components, but do not preclude the presence or addition of one or more other features, integers, steps, operations, elements, components, and/or groups thereof. It will also be understood, that when an element is referred to as being "connected" or "coupled" to another element, it can be directly connected or coupled to the other element but one or more intervening elements may also be present, unless expressly stated otherwise. Furthermore, "connected" or "coupled" as used herein may include wirelessly connected or coupled. As used herein, the term "and/or" includes any and all combinations of one or more of the associated listed items. The steps of any disclosed method is not limited to the exact order stated herein, unless expressly stated otherwise.

It should be appreciated that reference throughout this specification to "one embodiment" or "an embodiment" or "an aspect" or features included as "may" means that a particular feature, structure or characteristic described in connection with the embodiment is included in at least one embodiment of the disclosure. Furthermore, the particular features, structures or characteristics may be combined as suitable in one or more embodiments of the disclosure. The previous description is provided to enable any person skilled in the art to practice the various aspects described herein. Various modifications to these aspects will be readily apparent to those skilled in the art, and the generic principles defined herein may be applied to other aspects.

The claims are not intended to be limited to the aspects shown herein, but is to be accorded the full scope consistent with the language of the claims, wherein reference to an element in the singular is not intended to mean "one and only one" unless specifically so stated, but rather "one or more." Unless specifically stated otherwise, the term "some" refers to one or more.

Accordingly, the scope should be judged in terms of the claims that follow.

The invention claimed is:

1. Ear probe assembly comprising:
   a housing structure having a proximal side and a distal side; and
   a plurality of transducers arranged in said housing structure, said plurality of transducers including a first transducer comprising a first sound port and a second transducer comprising a second sound port,
   wherein respective longitudinal axes of said first and second sound ports are parallel to one another;
   wherein a channel structure comprises at least a first transducer entrance configured to receive said first sound port and a second transducer entrance configured to receive said second sound port, wherein said channel structure protrudes from said proximal side of said housing structure, and
   wherein said channel structure forms respective acoustic paths between said plurality of transducers and a tip portion of said ear probe, said tip portion being configured to connect with said channel structure,
   wherein said tip portion further comprises a set of integrated acoustic channels, wherein the set of integrated acoustic channels are configured to connect with said channel structure in a detachable manner,
   wherein the first transducer comprises a first membrane and the second transducer comprises a second membrane, wherein the first and second transducers are arranged in the housing structure, such that the first membrane lies substantially perpendicular to the second membrane, the first membrane substantially following the longitudinal axis of the first sound port, the second membrane following a direction perpendicular to the longitudinal axis of the second sound port,
   wherein the first and second transducers are arranged such that a bottom surface of the first transducer faces a top surface of the second transducer,
   wherein the channel structure comprises parallel channels corresponding to said first and second transducers, respectively,
   wherein each of the parallel channels
      shares a same longitudinal axis as the sound port of the corresponding transducer;
      comprises the transducer entrance of the corresponding transducer; and
      connects with a corresponding acoustic channel of said tip portion in a proximal end thereof,
   wherein a distal end of said channel structure is configured to receive said first and second sound ports of said first and second transducers.

2. Ear probe assembly according to claim 1, wherein a distal end of said first transducer is arranged to be substantially flush with a distal side of said second transducer.

3. Ear probe assembly according to claim 2, wherein a circuitry board in a top end of the housing structure is connected to a distal end of the first transducer and extends along the longitudinal direction of the housing to a bottom end of said second transducer, and circuitry on the circuitry board is connected to said second transducer.

4. Ear probe assembly according to claim 1, wherein a circuitry board of the housing structure is arranged so as to cover said first transducer and said second transducer.

5. Ear probe assembly according to claim 1, wherein the housing structure comprises a substantially flat surface area on said proximal side, wherein a distal side of said tip portion is configured to abut said substantially flat surface, and wherein said channel structure of said housing structure extends into said acoustic channels of the tip portion, such that at least a part of said channel structure is substantially contained in the tip portion.

6. Ear probe assembly according to claim 1, wherein a distance between a proximal surface and a distal surface of said tip portion defines a length of said tip portion, wherein said channel structure is extending into said tip portion so as to take up at least half of the length of said tip portion.

7. Ear probe assembly according to claim 1, wherein the channel structure is formed with a substantially triangular circumference, wherein the tip portion comprises a corresponding triangular opening configured to engage said triangular circumference of said channel structure in a detachable manner.

8. Ear probe assembly according to claim 1, wherein the channel structure comprises a first engagement structure configured to engage with a part of said housing structure on an inner side of the housing structure to lock the channel structure in said housing structure.

9. Ear probe assembly according to claim 1, wherein the channel structure further comprises a second engagement structure, said second engagement structure configured to engage with said tip portion.

10. Ear probe assembly according to claim 9, wherein the second engagement structure is formed as a protruding flange extending as a circular protrusion from said channel structure and configured to engage with a groove of said tip portion.

11. Ear probe assembly according to claim 1, wherein the first transducer is a microphone and the second transducer is a receiver.

12. Ear probe assembly according to claim 1, wherein the ear probe is configured to transmit an acoustic signal through one of said acoustic channels of said ear tip and to receive an acoustic signal through one of said acoustic channels and emitted by an auditory system of a test person.

13. Ear probe assembly according to claim 1, wherein said channel structure comprises at least two independent and acoustically separated acoustic paths, said acoustic paths each being configured to connect with at least two independent and acoustically separated acoustic channels of the tip portion.

14. Ear probe assembly according to claim 1, wherein an acoustic filter is arranged in each of said parallel channels of said channel structure to improve impulse response characteristics of the ear probe.

15. Ear probe assembly according to claim 1, wherein an exchangeable wax filter is arranged in each of said parallel channels of said channel structure.

\* \* \* \* \*